(12) United States Patent
Stadler et al.

(10) Patent No.: US 7,937,149 B2
(45) Date of Patent: *May 3, 2011

(54) METHOD AND APPARATUS FOR DETECTING CHANGE IN PHYSIOLOGIC PARAMETERS

(75) Inventors: Robert W. Stadler, Shoreview, MN (US); Karen J. Kleckner, New Brighton, MN (US); Robert T. Taepke, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 428 days.

This patent is subject to a terminal disclaimer.

(21) Appl. No.: 10/727,074

(22) Filed: Dec. 3, 2003

(65) Prior Publication Data

US 2005/0124900 A1      Jun. 9, 2005

(51) Int. Cl.
*A61N 1/365* (2006.01)

(52) U.S. Cl. .......................................... 607/17; 600/509

(58) Field of Classification Search .................. 607/5, 9, 607/17–21, 23–25; 600/508–509, 515–518
See application file for complete search history.

(56) References Cited

U.S. PATENT DOCUMENTS

| | | | |
|---|---|---|---|
| 3,744,480 A | 7/1973 | Gause et al. | 128/2.05 R |
| 4,360,030 A | 11/1982 | Citron et al. | |
| 4,374,382 A | 2/1983 | Markowitz | |
| 4,482,378 A | 11/1984 | Riou et al. | |
| 5,107,833 A | 4/1992 | Barness | |
| 5,117,824 A | 6/1992 | Keimel et al. | |
| 5,163,429 A * | 11/1992 | Cohen | 607/4 |
| 5,168,871 A | 12/1992 | Grevious | |
| 5,271,395 A | 12/1993 | Wahlstrand et al. | 607/9 |
| 5,292,343 A | 3/1994 | Blanchette et al. | |
| 5,314,450 A | 5/1994 | Thompson | |
| 5,318,597 A * | 6/1994 | Hauck et al. | 607/20 |
| 5,324,315 A | 6/1994 | Grevious | |
| 5,354,319 A | 10/1994 | Wyborny et al. | |
| 5,368,040 A | 11/1994 | Carney | |
| 5,383,909 A | 1/1995 | Keimel | |
| 5,535,752 A | 7/1996 | Halperin et al. | |
| 5,545,186 A | 8/1996 | Olson et al. | |

(Continued)

FOREIGN PATENT DOCUMENTS

WO    WO 2004/050178 A1    6/2004

OTHER PUBLICATIONS

U.S. Appl. No. 10/272,008, filed Dec. 3, 2003, "Method and Apparatus for Detecting Change in Intrathoracic Electrical Impedance".

*Primary Examiner* — Niketa I Patel
*Assistant Examiner* — Alyssa M Alter
(74) *Attorney, Agent, or Firm* — Michael C. Soldner

(57) ABSTRACT

A method and apparatus for detection of changes in physiologic parameters of a patient that includes generating measured physiologic parameters, generating an adaptive baseline trend of the measured physiologic parameters corresponding to a first time period, generating a short term trend of the measured physiologic parameters corresponding to a second time period less than the first time period, and generating a metric of physiologic parameter change between the adaptive baseline trend and one of a most recent measured physiologic parameter and the short term trend of the measured physiologic parameters.

6 Claims, 15 Drawing Sheets

U.S. PATENT DOCUMENTS

| | | | |
|---|---|---|---|
| 5,649,968 A | 7/1997 | Alt et al. .................... 607/19 |
| 5,755,736 A | 5/1998 | Gillberg et al. |
| 5,836,975 A | 11/1998 | DeGroot |
| 5,957,861 A | 9/1999 | Combs et al. |
| 6,102,874 A | 8/2000 | Stone et al. |
| 6,155,267 A | 12/2000 | Nelson |
| 6,508,771 B1 * | 1/2003 | Padmanabhan et al. ...... 600/515 |
| 6,580,946 B2 | 6/2003 | Struble |
| 6,671,549 B2 * | 12/2003 | Van Dam et al. ............. 607/25 |
| 2001/0027266 A1 * | 10/2001 | Hautala et al. ................ 600/16 |
| 2003/0220580 A1 | 11/2003 | Alt ............... 600/547 |
| 2004/0116819 A1 * | 6/2004 | Alt ............... 600/513 |
| 2004/0172080 A1 * | 9/2004 | Stadler et al. ................ 607/17 |

* cited by examiner

FIG. 9: Step 802 - Fast Adaptation of BL and STA

FIG. 10: Step 814 - Update STA

FIG. 11: Step 816 - Update BL

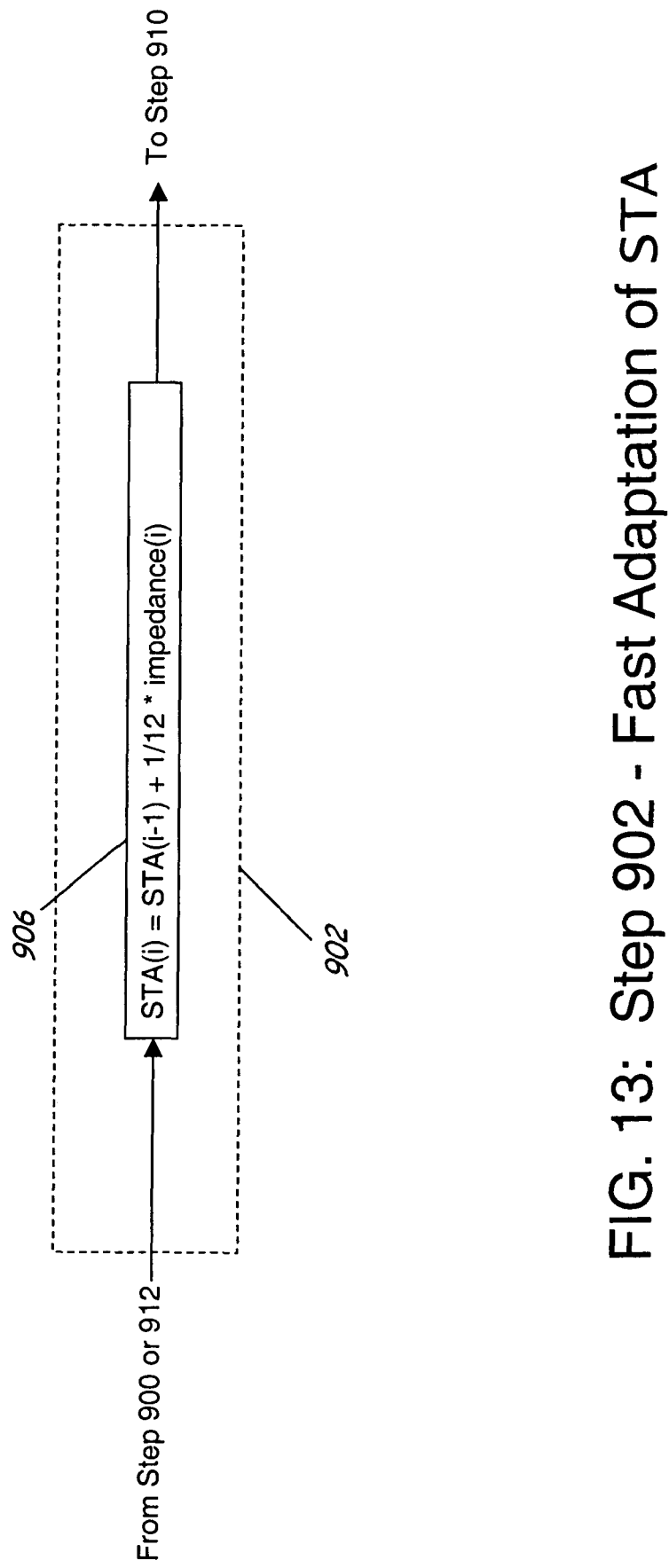
FIG. 13: Step 902 - Fast Adaptation of STA

METHOD AND APPARATUS FOR DETECTING CHANGE IN PHYSIOLOGIC PARAMETERS

CROSS-REFERENCE TO RELATED APPLICATION

Cross-reference is hereby made to a commonly assigned related U.S. application Ser. No. 10/727,008, filed concurrently herewith entitled "METHOD AND APPARATUS FOR DETECTING CHANGE IN INTRATHORACIC ELECTRICAL IMPEDANCE", by Robert W. Stadler and Li Wang, incorporated herein by reference in its entirety.

FIELD OF THE INVENTION

The present invention generally relates to implantable medical devices, and in particular, the present invention relates to monitoring of a physiologic parameter in an implantable medical device to determine physiological conditions in a patient.

BACKGROUND OF THE INVENTION

Various implantable medical devices are available for use in monitoring various physiological parameters. For example, U.S. Pat. No. 4,360,030 to Citron et al., entitled, "Apparatus For Monitoring And Storing A Variety Of Heart Activity Signals," issued Nov. 23, 1982, describes a heart monitoring and storing apparatus for evaluating heart activity signals. Further, for example, U.S. Pat. No. 5,535,752 to Halperin et al., entitled, "Implantable Capacitive Absolute Pressure And Temperature Monitor System," issued Jul. 16, 1996, describes a monitor that powers a sensor and which demodulates and stores absolute pressure and temperature data derived from signals generated by the sensor. Generally, an implantable device used for monitoring receives sensor output signals from one or more sensors, and monitors, records, and stores data representative of such signals when the device is implanted in a body and is operational. In addition, an implantable medical device used for monitoring includes transmitter/receiver circuitry for communicating information between the implanted device and a device external to the body, such as a programmer or external monitor.

Implantable monitoring devices, whether used solely as a monitoring device or in combination with other implantable therapeutic implantable devices, generally receive analog information from a sensor, store such information, and then transmit the stored information for use external to the body. For example, a monitor may collect information regarding various physiological parameters of a patient such that a physician may scan records containing such information when the collected information is transmitted external to the body. The physician may then appropriately diagnose and treat the patient, e.g., assess changes in patient status, provide a therapy plan for the patient, recognize trends in such data, etc.

Generally, the most common method for storing and/or transmitting such sensor information is to first digitize the sensor information representative of one or more physiological parameters (i.e., change the analog signal to digital format) and then provide for storage of the digitized information in such a format. For example, as described in U.S. Pat. No. 5,535,752, a capacitive pressure sensing lead is employed with an implantable battery-powered monitor, including a microprocessor for implementing demodulation, data storage, and telemetry capabilities. The monitor samples and stores blood pressure data at programmed intervals and telemeters out the accumulated data to an external programmer on receipt of a command from an external device, such as in a manner which is conventional in implantable medical device technology. The monitor performs such periodic storage of digitized data related to physiological parameters, such as blood pressure and temperature, at a nominal sampling frequency which may be related to patient activity level. For example, such sampling frequency may be correlated to time and date and patient initiated event markers. As described in U.S. Pat. No. 5,535,752, blood pressure signals may be digitized and stored at a sample period of every 4 milliseconds or in other words, at a 256 Hz sampling frequency. Further, for example, blood temperature signals may be digitized and stored once every sensed heart depolarization cycle. The digitized data values may be stored on a first-in first-out (FIFO) basis between periodic transmission of such data for permanent external storage outside of the device. External to the body, the data may then be analyzed to identify the portions of interest and to perform other diagnostic analysis of the accumulated data.

However, while collecting and storing data for later communication to an external device, such as a programmer, so that the data can then be utilized to subsequently inform a clinician of a patient's physiologic status over time, greater value could be obtained through an automated processing of physiologic parameters to highlight clinically significant changes in the parameters.

BRIEF DESCRIPTION OF THE DRAWINGS

Other aspects and features of the present invention will be readily appreciated as the same becomes better understood by reference to the following detailed description when considered in connection with the accompanying drawings, in which like reference numerals designate like parts throughout the figures thereof and wherein:

FIG. 13 is an exemplary schematic diagram illustrating obtaining initial short term average measurement values, according to an embodiment of the present invention.

DESCRIPTION OF EMBODIMENTS OF THE INVENTION

Figure 1:
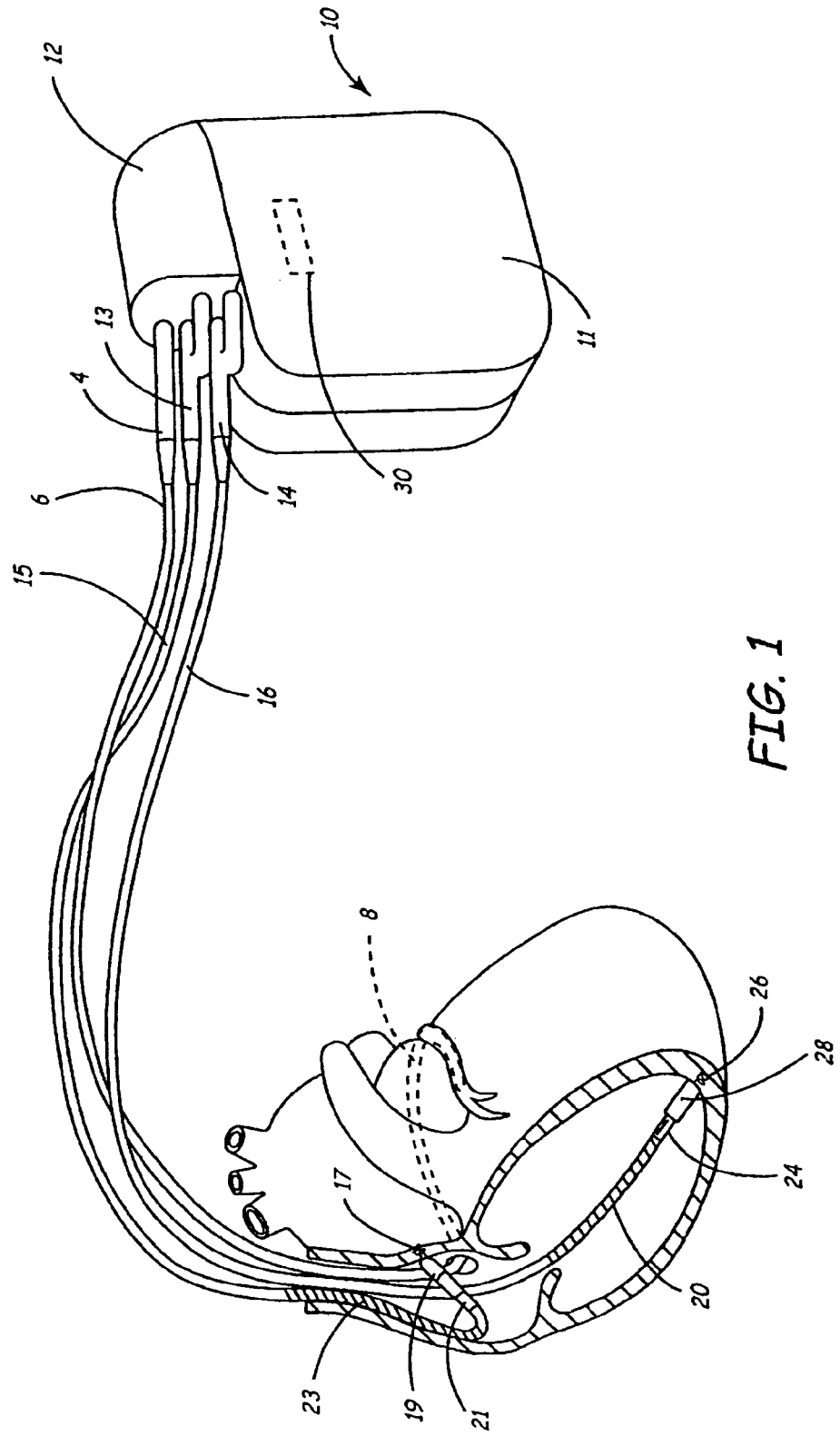
FIG. 1 is a schematic exemplary diagram of an implantable pacemaker/cardioverter/defibrillator of a type in which the present invention may usefully be practiced.

FIG. 1 is a schematic exemplary diagram of a pacemaker/cardioverter/defibrillator of a type in which the present invention may usefully be practiced. As illustrated in FIG. 1, an implantable medical device 10 of a type in which the present invention may usefully be practiced could be a pacemaker/cardioverter/defibrillator, for example, having a ventricular lead that includes an elongated insulative lead body 16, carrying three mutually insulated conductors. Located adjacent the distal end of the lead are a ring electrode 24, an extendable helix electrode 26, mounted retractably within an insulative electrode head 28, and an elongated coil electrode 20. Each of the electrodes is coupled to one of the conductors within the lead body 16. Electrodes 24 and 26 are employed for cardiac pacing and for sensing ventricular depolarizations. At the proximal end of the lead is a bifurcated connector 14, which carries three electrical connectors, each coupled to one of the coiled conductors.

An atrial/SVC lead includes an elongated insulative lead body 15, also carrying three mutually insulated conductors. Located adjacent the J-shaped distal end of the lead are a ring electrode 21 and an extendible helix electrode 17, mounted retractably within an insulative electrode head 19. Each of the electrodes is coupled to one of the conductors within the lead body 15. Electrodes 17 and 21 are employed for atrial pacing and for sensing atrial depolarizations. An elongated coil electrode 23 is provided, proximal to electrode 21 and coupled to the third conductor within the lead body 15. At the proximal end of the lead is a bifurcated connector 13, which carries three electrical connectors, each coupled to one of the coiled conductors.

Any other known lead configurations may also be utilized other the lead configuration of FIG. 1. For example, coil electrode 123 could be located on ventricular lead 105 and positioned within the atrium or SVC by ventricular lead 105 rather than by atrial lead 107.

A coronary sinus lead includes an elongated insulative lead body 6, carrying one conductor, coupled to an elongated coiled defibrillation electrode 8. Electrode 8, illustrated in broken outline, is located within the coronary sinus and great vein of the heart. At the proximal end of the lead is a connector plug 4 which carries an electrical connector, coupled to the coiled conductor.

The pacemaker/cardioverter/defibrillator 10 includes a hermetic enclosure 11 containing the electronic circuitry used for generating cardiac pacing pulses for delivering cardioversion and defibrillation shocks and for monitoring the patient's heart rhythm. Pacemaker/cardioverter/defibrillator 10 is shown with the lead connector assemblies 4, 13 and 14 inserted into the connector block 12, which serves as a receptacle and electrical connector for receiving the connectors 4, 13 and 14 and interconnecting the leads to the circuitry within enclosure 11. An activity sensor 30 is illustrated schematically by broken outline, and may be an accelerometer or a piezoelectric transducer. Sensor 30 may be used for regulation of pacing rate based upon demand for cardiac output.

Optionally, insulation of the outward facing portion of the housing 11 of the pacemaker/cardioverter/defibrillator 10 may be provided or the outward facing portion may instead be left uninsulated, or some other division between insulated and uninsulated portions may be employed. The uninsulated portion of the housing 11 optionally serves as a subcutaneous defibrillation electrode, used to defibrillate either the atria or ventricles. Other lead configurations and electrode locations may of course be substituted for the lead set illustrated. For example, atrial defibrillation and sensing electrodes might be added to either the coronary sinus lead or the right ventricular lead instead of being located on a separate atrial lead, allowing for a two lead system.

Figure 2:
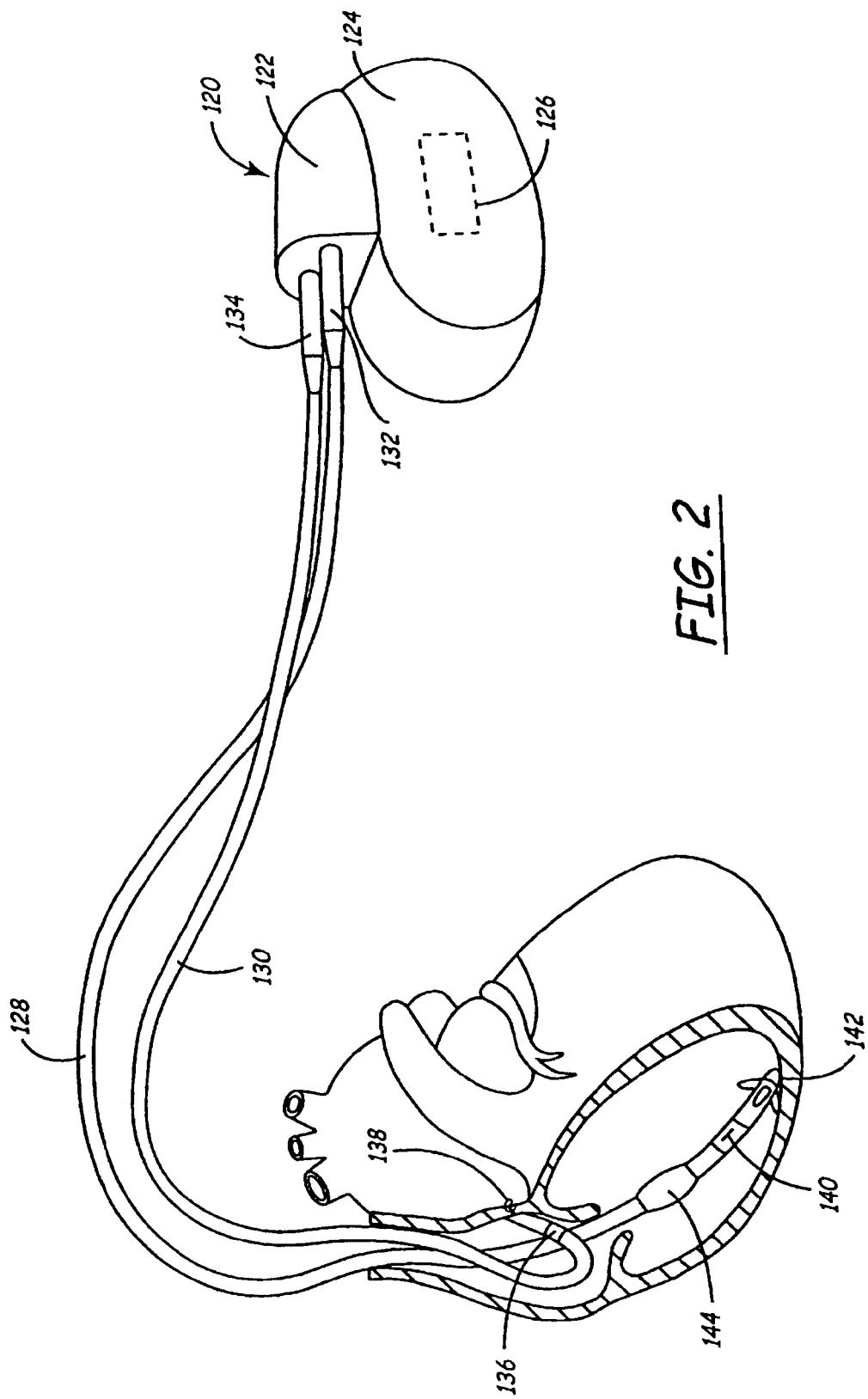
FIG. 2 is a schematic exemplary diagram of an implantable pacemaker of a type in which the present invention may usefully be practiced.

FIG. 2 is a schematic exemplary diagram of an implantable pacemaker of a type in which the present invention may usefully be practiced. As illustrated in FIG. 2, a pacemaker 120 includes a hermetic enclosure 124 containing the electronic circuitry used for generating cardiac pacing pulses and for monitoring the patient's heart rhythm. An activity sensor 126 is illustrated schematically by broken outline, and may be an accelerometer or a piezoelectric transducer as discussed above in conjunction with FIG. 1. Mounted to the enclosure 124 is a header 122 which serves as a receptacle and electrical connector for receiving the connectors 132 and 134 of pacing leads 128 and 130 and interconnecting the leads to the circuitry within enclosure 124. Lead 128 is a ventricular lead provided with electrodes 140 and 142 for monitoring right ventricular heart signals. Also illustrated on lead 128 is a physiologic sensor 144 which may optionally be included in addition to or as an alternative to the activity sensor 126, and which may take the form of an oxygen sensor, pressure sensor, temperature sensor, other sensor of any of the various types employed for monitoring demand for cardiac output or for measuring heart hemodynamics. Sensor 144 may be used in conjunction with or as an alternative to the activity sensor 126 for rate responsive pacing. Atrial lead 130 carries electrodes 136 and 138 and is employed for sensing and pacing the patient's atrium.

Figure 3:
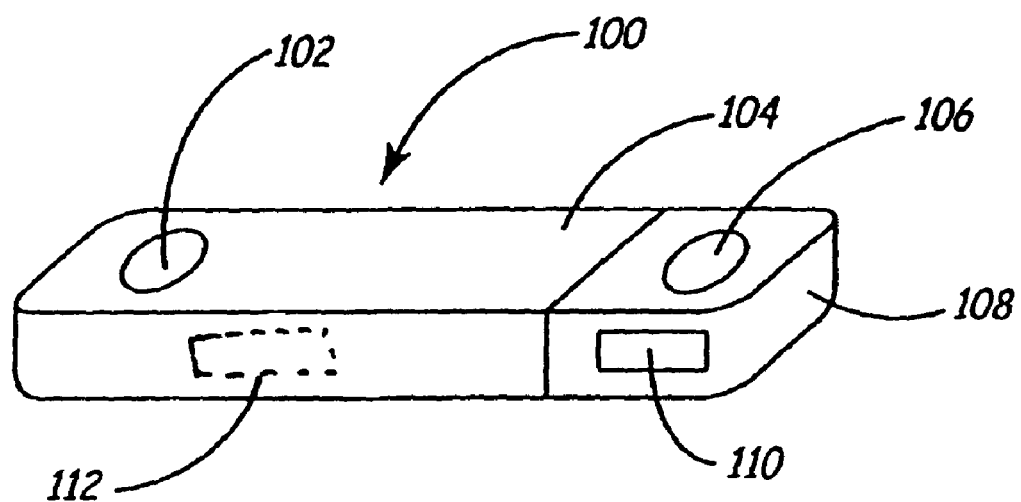
FIG. 3 is a functional schematic diagram of an implantable monitor of a type in which the present invention may usefully be practiced.

FIG. 3 is a functional schematic diagram of an implantable monitor of a type in which the present invention may usefully be practiced. As illustrated in FIG. 3, an exemplary implantable monitor in which the present invention may usefully be practiced includes a hermetically sealed enclosure 104 containing the electronic circuitry used for generating cardiac pacing pulses and for monitoring the patient's heart rhythm and which carries a molded plastic header 108. The enclosure 104 and the header 108 each carry an electrode 102 and 106, respectively for monitoring heart rhythm. Also mounted in the header 108 is an antenna 110 for use in communicating between the device and an external programmer. Illustrated in broken outline at 112 is an internal activity sensor, of the type typically employed in the context of rate responsive cardiac pacemakers, taking the form either of an accelerometer or a piezo-electric transducer. Heart signals are detected between the electrodes 102 and 106 and measurements of physical activity are detected by sensor 112 for storage and analysis.

Figure 4:
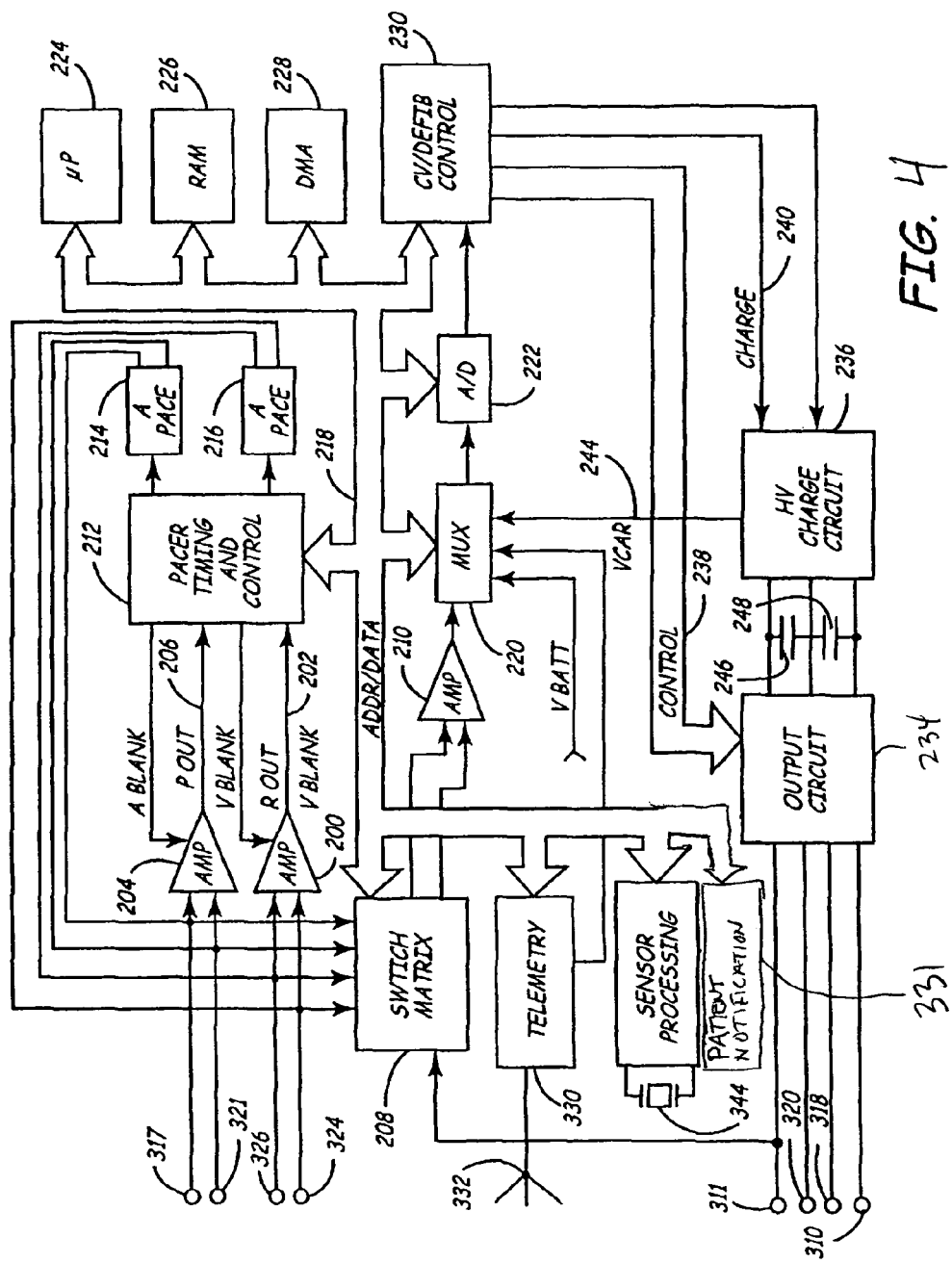
FIG. 4 is a functional block diagram of an implantable pacemaker/cardioverter/defibrillator of a type in which the present invention may usefully be practiced.

FIG. 4 is a functional block diagram of an implantable pacemaker/cardioverter/defibrillator of a type in which the present invention may usefully be practiced. This diagram should be taken as exemplary of one type of anti-tachyarrhythmia device in which the invention may be embodied, and not as limiting, as it is believed that the invention may usefully be practiced in a wide variety of device implementations, including devices providing therapies for treating atrial arrhythmias instead of or in addition to ventricular arrhythmias, cardioverters and defibrillators which do not provide anti-tachycardia pacing therapies, anti-tachycardia pacers which do not provide cardioversion or defibrillation, and devices which deliver different forms of anti-arrhythmia therapies such nerve stimulation or drug administration.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to electrode 11, and is the uninsulated portion of the housing of the implantable pacemaker/cardioverter/defibrillator. Electrode 320 corresponds to electrode 20 and is a defibrillation electrode located in the right ventricle. Electrode 310 corresponds to electrode 8 and is a defibrillation electrode located in the coronary sinus. Electrode 318 corresponds to electrode 23 and is a defibrillation electrode located in the superior vena cava. Electrodes 324 and 326 correspond to electrodes 24 and 26, and are used for sensing and pacing in the ventricle. Electrodes 317 and 321 correspond to electrodes 19 and 21 and are used for pacing and sensing in the atrium.

Electrodes 310, 311, 318 and 320 are coupled to high voltage output circuit 234. Electrodes 324 and 326 are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 324 and 326 exceeds the present sensing threshold.

Electrodes 317 and 321 are coupled to the P-wave amplifier 204, which preferably also takes the form of an automatic gain controlled amplifier providing an adjustable sensing threshold as a function of the measured R-wave amplitude. A signal is generated on P-out line 206 whenever the signal sensed between electrodes 317 and 321 exceeds the present sensing threshold. The general operation of the Rwave and P-wave amplifiers 200 and 204 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety. However, any of the numerous prior art sense amplifiers employed in implantable cardiac pacemakers, defibrillators and monitors may also usefully be employed in conjunction with the present invention.

Switch matrix 208 is used to select which of the available electrodes are coupled to wide band amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

Telemetry circuit 330 receives downlink telemetry from and sends uplink telemetry to the patient activator by means of antenna 332. Data to be uplinked to the activator and control signals for the telemetry circuit are provided by microprocessor 224 via address/data bus 218. Received telemetry is provided to microprocessor 224 via multiplexer 220. The atrial and ventricular sense amp circuits 200, 204 produce atrial and ventricular EGM signals, which also may be digitized and uplink telemetered to an associated programmer on receipt of a suitable interrogation command. The device may also be capable of generating so-called marker codes indicative of different cardiac events that it detects. A pacemaker with marker-channel capability is described, for example, in U.S. Pat. No. 4,374,382 to Markowitz, which patent is hereby incorporated by reference herein in its entirety. The particular telemetry system employed is not critical to practicing the invention, and any of the numerous types of telemetry systems known for use in implantable devices may be used. In particular, the telemetry systems as disclosed in U.S. Pat. No. 5,292,343 issued to Blanchette et al., U.S. Pat. No. 5,314,450, issued to Thompson, U.S. Pat. No. 5,354,319, issued to Wyborny et al. U.S. Pat. No. 5,383, 909, issued to Keimel, U.S. Pat. No. 5,168,871, issued to Grevious, U.S. Pat. No. 5,107,833 issued to Barsness or U.S. Pat. No. 5,324,315, issued to Grevious, all incorporated herein by reference in their entireties, are suitable for use in conjunction with the present invention. However, the telemetry systems disclosed in the various other patents cited herein which are directed to programmable implanted devices, or similar systems may also be substituted. The telemetry circuit 330 is of course also employed for communication to and from an external programmer, as is conventional in implantable anti-arrhythmia devices.

The device of FIG. 4 may additionally is provided with an activity sensor 344, mounted to the interior surface of the device housing or to the hybrid circuit within the device housing. The sensor 344 and sensor present in circuitry 342 may be employed in the conventional fashion described in U.S. Pat. No. 4,428,378 issued to Anderson et al, incorporated herein by reference in its entirety, to regulate the underlying pacing rate of the device in rate responsive pacing modes.

A patient notification circuit 331 enables the patient to be notified in the event that it is determined that a significant change in a physiologic parameter has occurred, as will be in detail described below.

The remainder of the circuitry is dedicated to the provision of cardiac pacing, cardioversion and defibrillation therapies, and, for purposes of the present invention may correspond to circuitry known in the prior art. An exemplary apparatus is disclosed for accomplishing pacing, cardioversion and defibrillation functions as follows. The pacer timing/control circuitry 212 includes programmable digital counters which control the basic time intervals associated with DDD, WI, DVI, VDD, AAI, DDI, DDDR, VVIR, DVIR, VDDR, AAIR, DDIR and other modes of single and dual chamber pacing well known to the art. Circuitry 212 also controls escape intervals associated with anti-tachyarrhythmia pacing in both the atrium and the ventricle, employing, any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by signals on lines 202 and 206, and in accordance with the selected mode of pacing on time-out trigger generation of pacing pulses by pacer output circuits 214 and 216, which are coupled to electrodes 317, 321, 324 and 326. The escape interval counters are also reset on generation of pacing pulses, and thereby control the basic timing of cardiac pacing functions, including anti-tachyarrhythmia pacing.

The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, PR intervals and R-P intervals, which measurements are stored in memory 226 and are used in conjunction with the present invention to measure heart rate variability and in conjunction with tachyarrhythmia detection functions.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. Microprocessor 224 includes associated ROM in which the stored program controlling its operation as described below resides. A portion of the memory 226 (FIG. 2) may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

The arrhythmia detection method of the present invention may include any of the numerous available prior art tachyarrhythmia detection algorithms. One preferred embodiment may employ all or a suset of the rule-based detection methods described in U.S. Pat. No. 5,545,186 issued to Olson et al. or in U.S. Pat. No. 5,755,736 issued to Gillberg et al., both incorporated herein by reference in their entireties. However, any of the various arrhythmia detection methodologies known to the art might also usefully be employed in alternative embodiments of the invention.

In the event that an atrial or ventricular tachyarrhythmia is detected, and an anti-tachyarrhythmia pacing regimen is desired, timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters.

In the event that generation of a cardioversion or defibrillation pulse is required, microprocessor 224 employs the escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization. In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse.

Figure 5:
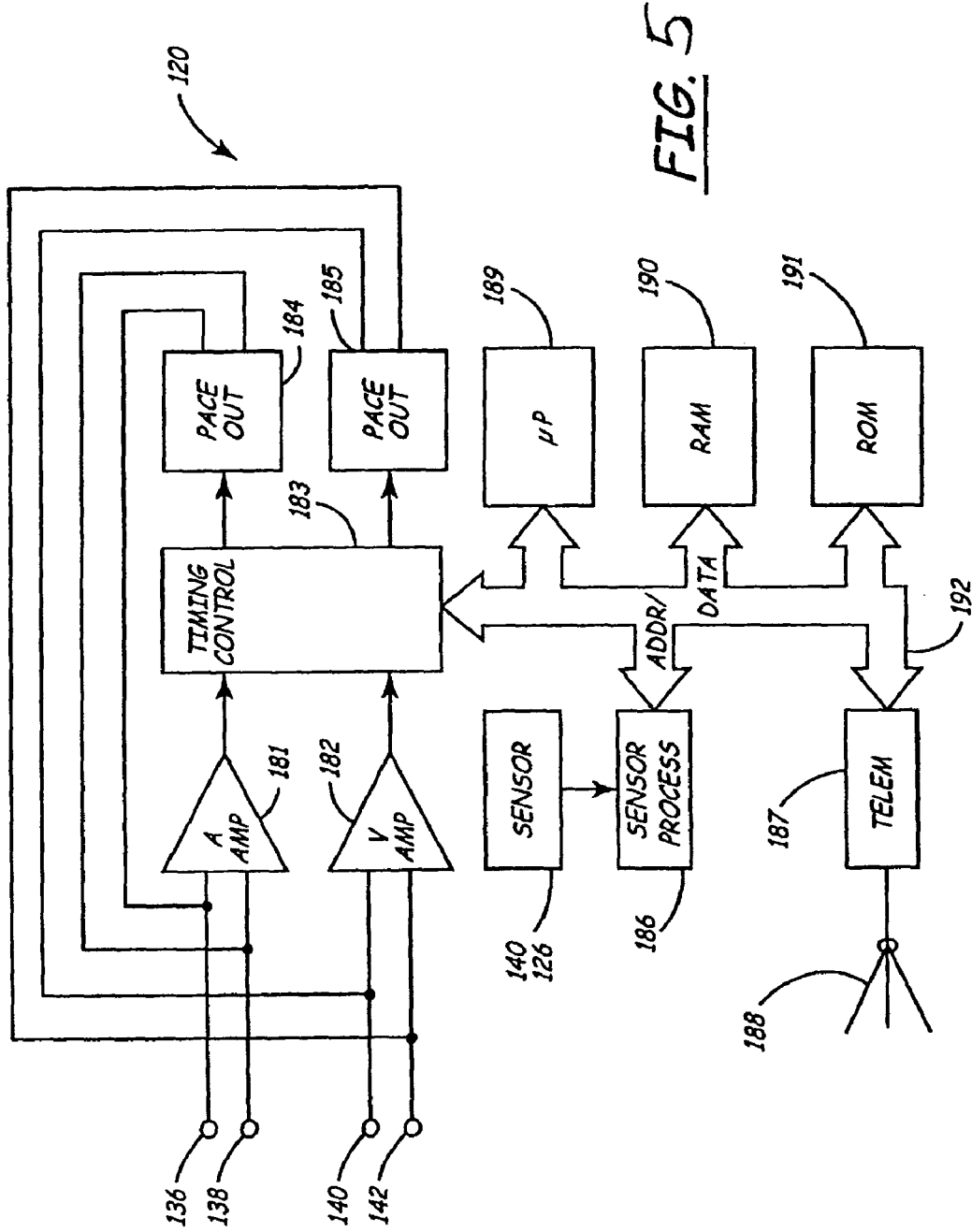
FIG. 5 is a functional block diagram of an implantable pacemaker of a type in which the present invention may usefully be practiced.

FIG. 5 is a functional block diagram of an implantable pacemaker of a type in which the present invention may usefully be practiced. The pacemaker of FIGS. 2 and 5 is essentially a set of subcomponents of the implantable pacemaker/cardioverter/defibrillator illustrated in FIGS. 1 and 4. Like the device of FIG. 4, the pacemaker is a microprocessor controlled device with microprocessor 189 operating under control of programming stored in Read Only Memory (ROM) 191. In the device as illustrated, electrodes 136 and 138, intended for location in the atrium of the patient's heart are coupled to an atrial amplifier 181 which may correspond to atrial amplifier 204 in FIG. 4. Similarly, ventricular electrodes 140 and 142 are coupled to ventricular amplifier 182, which may correspond to ventricular amplifier 200 in FIG. 4. The outputs of atrial and ventricular amplifiers 181 and 182 are input into timing and control circuitry 183 which conforms generally to the pacer timing and control circuitry 212 of FIG. 4, and which measures intervals between detected depolarizations and controls intervals between delivered pacing pulses as well as generating interrupts via data/address 192 to awake microprocessor 189 in response to delivery of a pacing pulse or sensing of a cardiac depolarization. Intervals between depolarizations measured by timing control circuitry 183 are stored in Random Access Memory (RAM) 190 until processed by microprocessor 189 to derive average heart rate values. Atrial and ventricular pacing pulses delivered according to one or more of the standard pacing modes described in conjunction with FIG. 4 are produced by atrial and ventricular pulse generator circuits 184 and 185 which may correspond to pulse generator circuits 215 ad 216 in FIG. 4.

The sensor illustrated in FIG. 5 may correspond to either an activity sensor 126 as described in conjunction with FIG. 2 above or to a hemodynamic sensor 140, as described in conjunction with FIG. 2. If the sensor is an activity sensor, then sensor processing circuitry 186 may correspond to sensor processing circuitry 342 discussed in conjunction with FIG. 4. However, if the sensor is a hemodynamic sensor, the sensor processing circuitry would correspond to the sort of processing circuitry typically associated with hemodynamic sensors. Telemetry circuitry 187 in conjunction with antenna 188 serves to transmit information to and receive information from an external programmer precisely as described above in conjunction with the device of FIG. 4, including information related to stored median interval values and heart rate variability measurements in RAM 190, as calculated by microprocessor 189.

Figure 6:
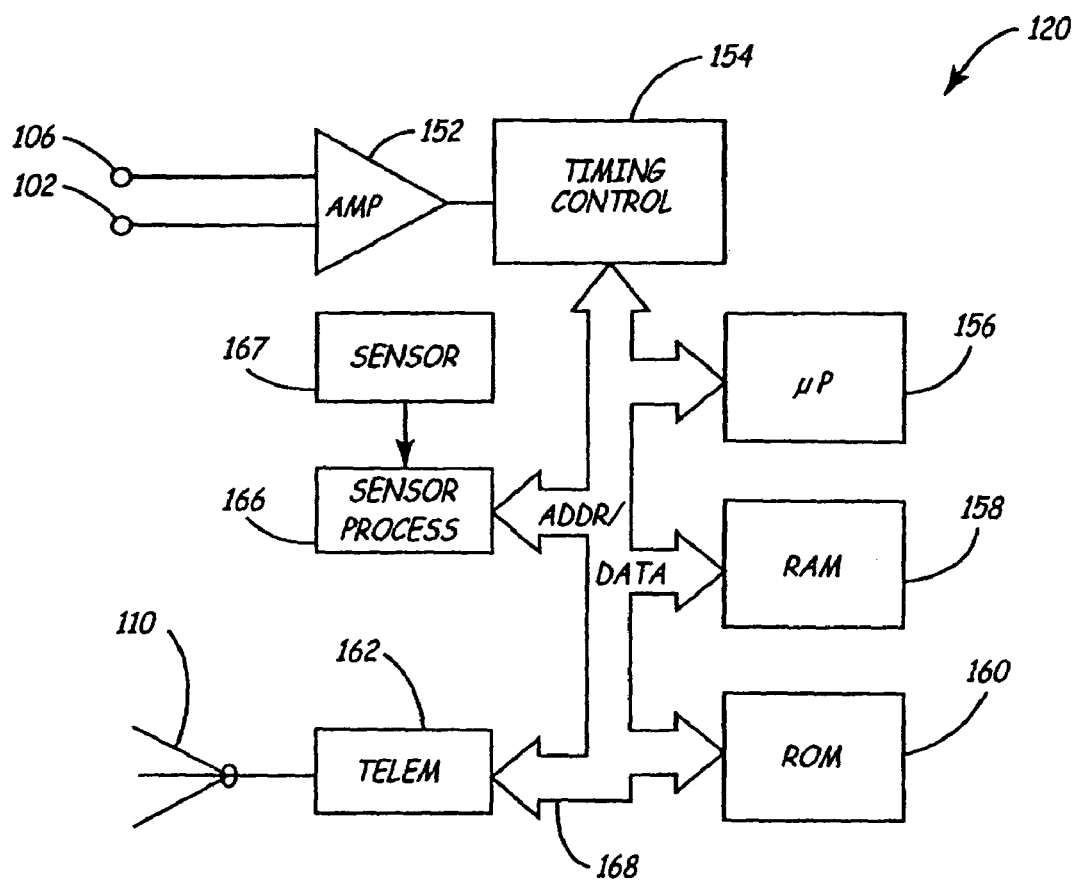
FIG. 6 is a functional block diagram of an implantable monitor of a type in which the present invention may usefully be practiced.

FIG. 6 is a functional block diagram of an implantable monitor of a type in which the present invention may usefully be practiced. FIG. 6 illustrates the functional organization of the subcutaneously implantable heart monitor 100 illustrated in FIG. 3. This device consists essentially of a set of subcomponents of the more complex embodiment of the invention disclosed in FIG. 4, and includes a sense amplifier 152 coupled to electrodes 102 and 106, illustrated in FIG. 1. Sense amplifier 152 may correspond to sense amplifier 204 or 200 in FIG. 4. Like the device of FIG. 4, the implantable monitor may be a microprocessor control device operating under control microprocessor 156 with its functionality controlled primarily by software stored in the read only memory associated therein. In this context, amplifier 152 detects the occurrence of heart depolarizations, with timing/control circuitry 154 serving to measure the durations between the detected heart depolarizations and to generate interrupts awakening microprocessor 156 so that it may store, analyze and process the detected intervals. Random Access Memory (RAM) 158 serves to store measured and calculated parameters including the calculated median heart rate and/or heart rate variability values for later telemetry to an external device. Like the device in FIG. 4, timing and control circuitry communicates with the microprocessor and the remaining circuitry by means of the address/data bus 168. Telemetry system 162 may correspond to telemetry system 330 in FIG. 4 and, via antenna 110 transmits and receives information from the external programmer, including transmitting information with regard to the calculated median rate values and heart variability values stored in RAM 158. Sensor 112 may correspond to sensor 344 in FIG. 4 and it may be a physical activity sensor as discussed above. The output of sensor 112 is passed through sensor processing circuitry 166 which may correspond to sensor processing circuitry 342 in FIG. 4.

Figure 7A:
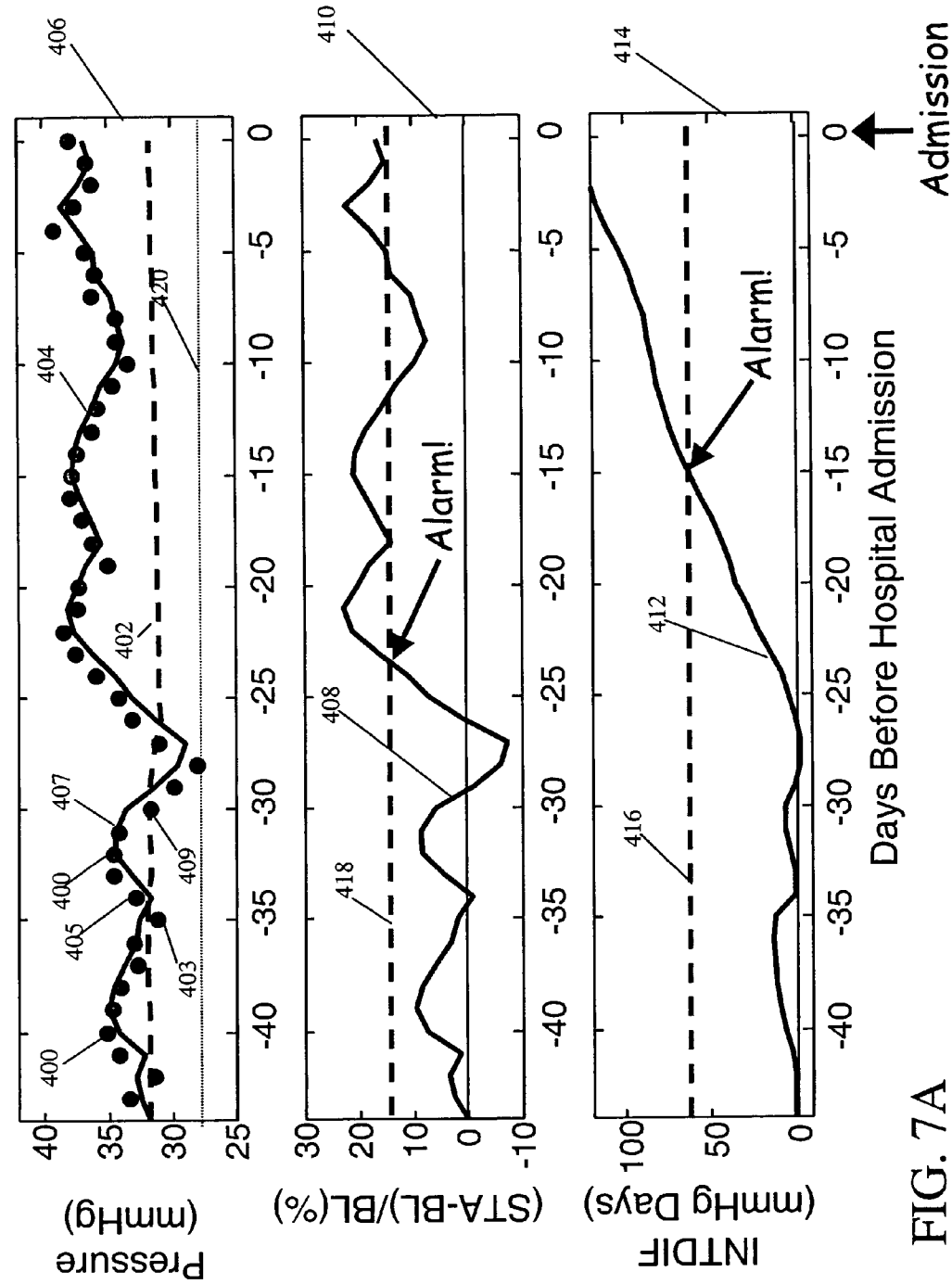
FIGS. 7A-7C are graphical representations of exemplary physiological data generated according to an embodiment of the present invention.
Figure 7B:
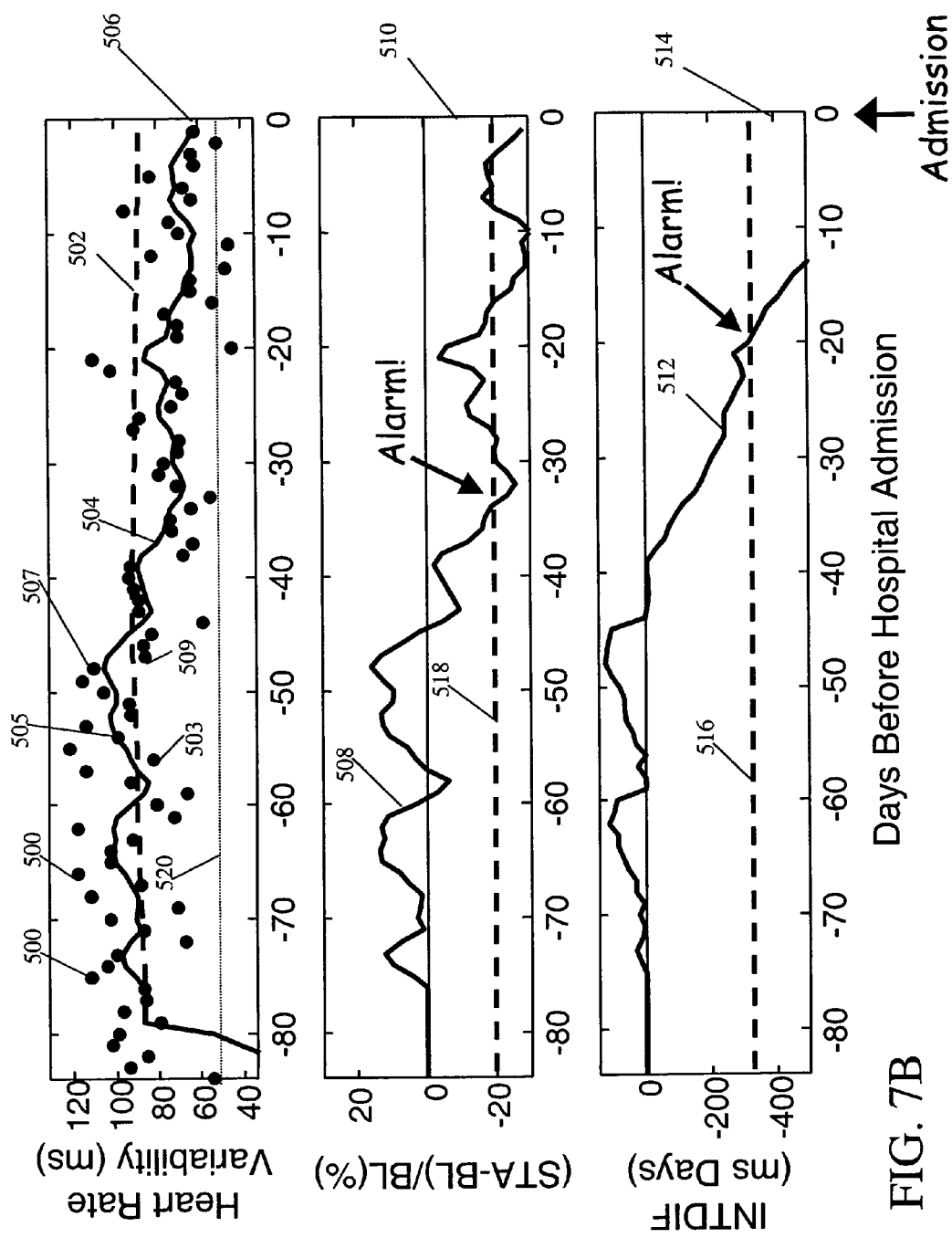
Figure 7C:
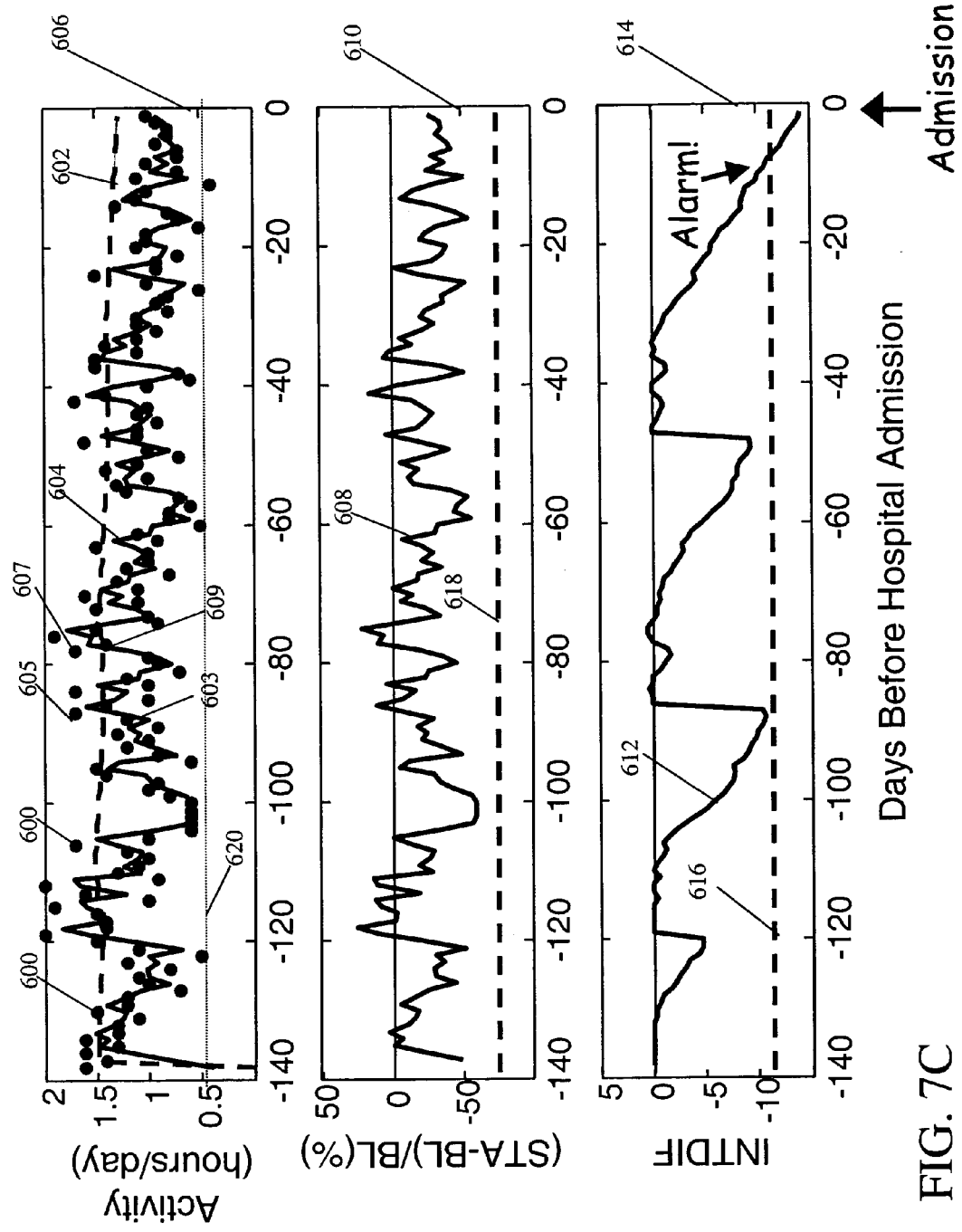

FIGS. 7A-7C are graphical representations of exemplary physiological data generated according to an embodiment of the present invention. According to the present invention, using the resulting physiological measurements generated using an implantable medical device, such as one of those described above, for example, a parameter corresponding to physiological measurements, such as pressure, heart rate variability, activity level, acquired over a predetermined time period is calculated and utilized to obtain a corresponding physiologic parameter. Values of a corresponding expected physiologic measurement and a short term average (STA) measurement are computed from the physiologic parameter, and changes in the physiologic parameter over time are monitored for indications of heart failure decompensations, as will be described below.

The expected physiological measurement is an underlying baseline (BL) measurement that is a very low pass filtered version of the physiologic parameter, and is intended to represent the patient's healthy physiologic measurement associated with the patient having no indication of heart failure decompensation present. The value of an expected or baseline measurement generally varies from patient to patient. For example, a pressure parameter, such as the estimated pulmonary artery diastolic (ePAD) pressure is generally between approximately 10 mmHG and 40 mmHG (FIG. 7A), a heart rate variability (HRV) parameter is generally between approximately 60 ms and 120 ms (FIG. 7B), and an activity level parameter is generally between approximately 0.5 hours/day and 2 hours/day (FIG. 7C). The short term average (STA) measurement is a slightly filtered version of the physiologic parameter, and is intended to be a best estimate of the current physiological measurement associated with the given physiologic parameter.

For example, as illustrated in FIG. 7A, according to an embodiment of the present invention in which the physiologic parameter is generated from pressure measurements obtained by the implantable medical device, a graphical representation of calculated pressure parameters 400, each corresponding to individual pressure measurements collected a predetermined number of times per day during a predetermined period of the day are generated in plot 406 from pressure measurements generated using known pressure measurement techniques, such as described, for example, in commonly assigned U.S. Pat. No. 5,368,040 to Carney. and U.S. Pat. No. 6,580,946 to Struble, both incorporated herein by reference in their entireties. In the example illustrated in FIG. 7A, each pressure parameter 400 corresponds to the median of estimated pulmonary artery diastolic (ePAD) pressures collected over a 24 hour period, although it is understood that other methods for generating pressure parameters 400 could also be utilized. In addition, calculated values of a baseline pressure measurement 402 and a short term average (STA) pressure measurement 404, shown by a hashed line and a solid line, respectively, are also generated, as will be described below.

In addition, a graphical representation of the difference between the calculated short term average pressure measurement and the calculated baseline pressure measurement as a percentage of the baseline measurement 408 is generated in plot 410, and a graphical representation of the integral of the difference (IntDiff) 412 illustrated by the difference between the baseline pressure measurement 402 and the pressure parameter 400 is generated in plot 414. The integral of the difference (IntDiff) 412 accumulates the difference between baseline pressure measurement 402 and the calculated pressure parameters 400, as will be described below.

According to another embodiment of the present invention, as illustrated in FIG. 7B, in which the physiologic parameter is generated from heart rate variability measurements obtained by the implantable medical device, a graphical representation of calculated heart rate variability (HRV) parameters 500, each corresponding to a heart rate variability calculated over a predetermined period of time are generated in plot 506 from heart rate intervals generated using known heart rate variability monitoring techniques, such as described, for example, in commonly assigned U.S. Pat. No. 6,508,771 to Padmanabhan et al., incorporated herein by reference in it's entirety. In addition, calculated values of a baseline HRV measurement 502 and a short term average (STA) HRV measurement 504, shown by a hashed line and a solid line, respectively, are also generated, as will be described below.

In addition, a graphical representation of the difference between the calculated short term average HRV measurement and the calculated baseline HRV measurement as a percentage of the baseline HRV measurement 508 is generated in plot 510, and a graphical representation of the integral of the difference (IntDiff) 512 illustrated by the difference between the baseline HRV measurement 502 and the HRV parameter 500 is generated in plot 514. The integral of the difference (IntDiff) 512 accumulates the difference between baseline HRV measurement 502 and the calculated HRV parameters 400, as will be described below.

According to another embodiment of the present invention, as illustrated in FIG. 7C, in which the physiologic parameter is generated from activity measurements obtained by the implantable medical device, a graphical representation of calculated activity level parameters 600, each corresponding to an activity level calculated over a predetermined period of time are generated in plot 606 from activity counts generated using known activity level monitoring techniques, such as described, for example, in commonly assigned U.S. Pat. No. 6,102,874 to Stone et al. incorporated herein by reference in it's entirety. In addition, calculated values of a baseline activity measurement 602 and a short term average (STA) activity measurement 604, shown by a hashed line and a solid line, respectively, are also generated, as will be described below.

In addition, a graphical representation of the difference between the calculated short term average activity measurement and the calculated baseline activity measurement as a percentage of the baseline activity measurement 608 is generated in plot 610, and a graphical representation of the integral of the difference (IntDiff) 612 illustrated by the difference between the baseline activity measurement 602 and the activity level parameter 600 is generated in plot 614. The integral of the difference (IntDiff) 612 accumulates the difference between baseline activity measurement 602 and the calculated activity level parameters 500, as will be described below.

Although the present invention is described using pressure, heart rate variability or activity levels to generate the parameter for monitoring heart failure decompensation, other physiologic parameters may also be utilized, such as pH, $O_2$ saturation, night heart rate, day heart rate, night/day heart rate ratio, systolic interval (STI), pre-ejection interval (PEI), temperature, cardiac accelerometer (contractility), heart rate turbulance, QT interval variability, for example.

Figure 8:
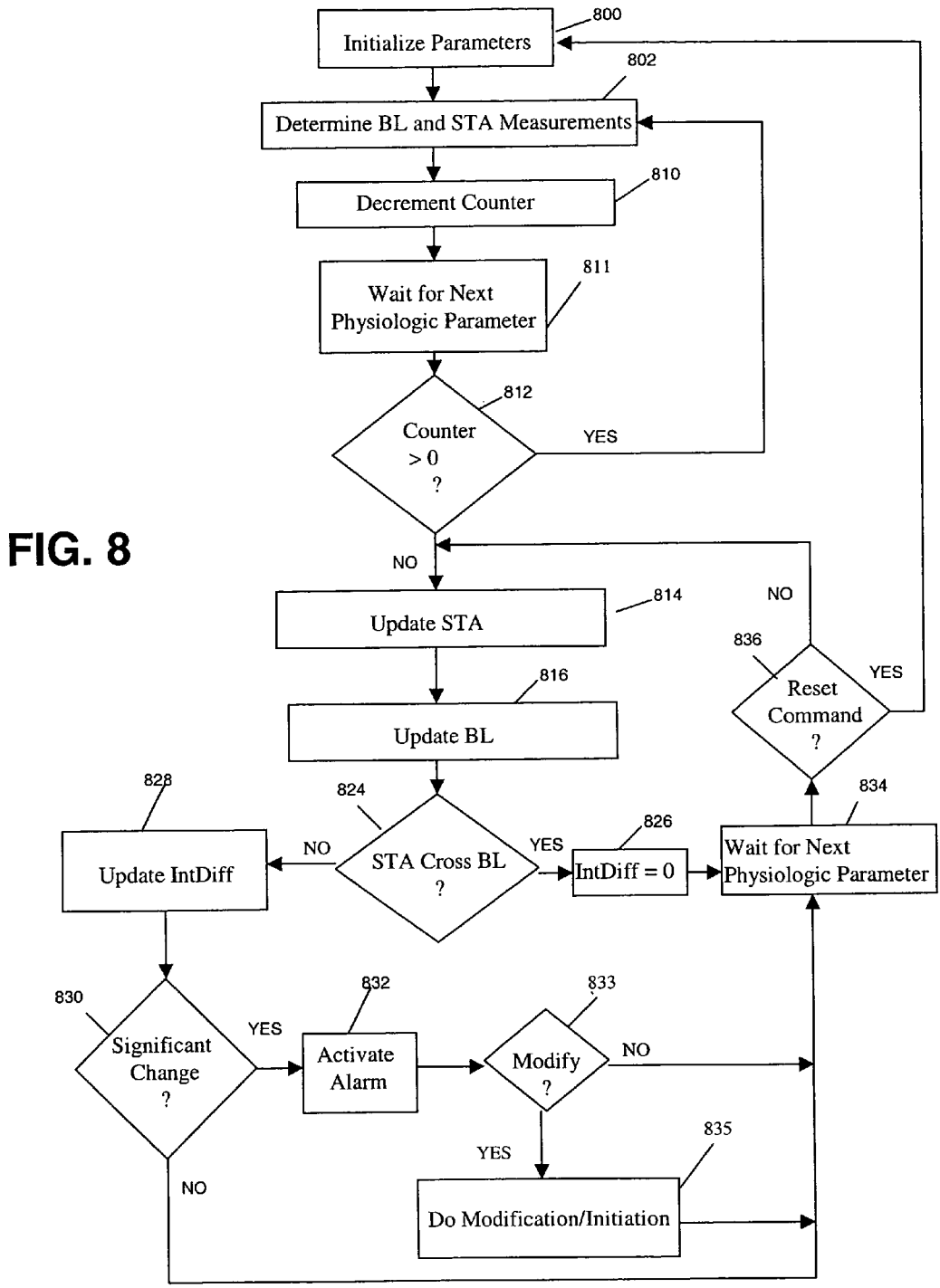
FIG. 8 is a flow chart illustrating a method for determining changes in a physiological parameter according to an embodiment of the present invention.

FIG. 8 is a flow chart illustrating a method for determining changes in a physiological parameter according to an embodiment of the present invention. Because of post-implant drop and recovery in the physiological parameters that typically occurs immediately after the device is implanted within the patient, the method for determining changes in a physiological parameter according to the present invention is not initiated until after a predetermined period of time subsequent to implantation of the device 100 within the patient has expired. An exemplary period post implant may be 30 days, for example, in order to allow for post-operative stabilization of the physiologic measurements before the algorithm is activated. Once the initial stabilization time period has expired, the algorithm establishes initial values of the expected, or baseline (BL) measurement, and the short term average (STA) measurement, and begins to search for changes in the physiological parameter obtained, i.e., pressure, heart rate variability, activity, etc.

As illustrated in FIG. 8, once the physiological parameter monitoring feature is initiated by microprocessor 224, microprocessor 224 initiates parameters for determining changes in the physiologic parameter according to the present invention by setting the baseline BL measurement, the short term average STA measurement, and the integral of the difference (IntDiff) between the baseline BL measurement and the calculated physiological parameter equal to zero, and setting a physiologic parameter measurement counter equal to a preset predetermined number of measurements, Step 800. The predetermined number of measurements is chosen according to the number of days that are desired for initiating the baseline measurement BL and the short term average measurement STA parameters. For example, in an embodiment in which pressure, heart rate variability or activity are utilized as the physiological measurement, the baseline BL measurement and the short term average measurement parameters are initiated over eight days, although it is understood that any desired number of days may be utilized.

Once the parameters have been initialized in Step 800, initial values of the baseline BL measurement and the short term average STA measurement are determined, Step 802, based on the calculated physiologic parameter generated a predetermined number of times over a period of days associated with the physiologic parameter measurement counter.

Figure 9:
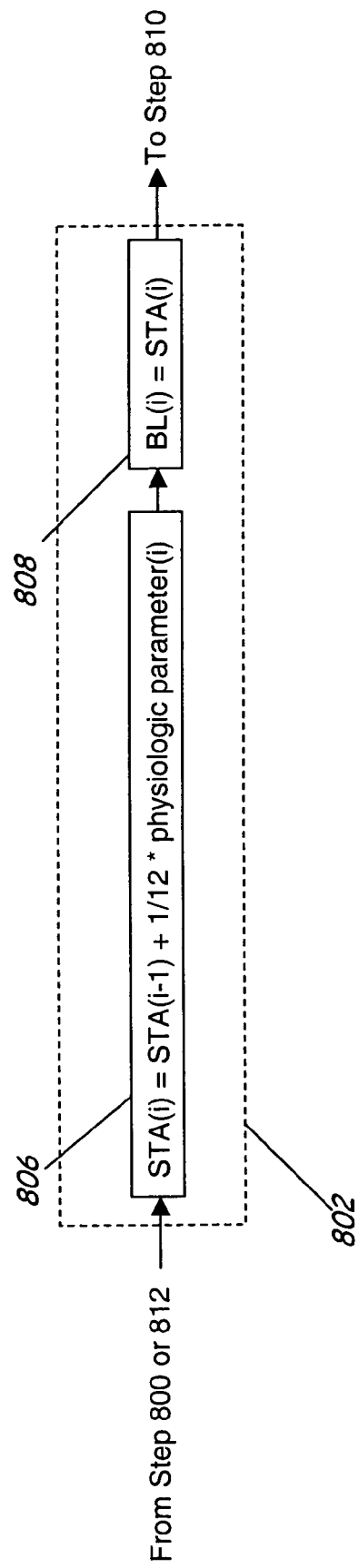
FIG. 9 is an exemplary schematic diagram illustrating obtaining initial baseline measurement and short term average measurement values, according to an embodiment of the present invention.

FIG. 9 is an exemplary schematic diagram illustrating obtaining initial baseline measurement and short term average measurement values, according to an embodiment of the present invention. In particular, as illustrated in FIGS. 8 and 9, in an embodiment of the present invention, the initial values for the baseline BL measurement and the short term average STA measurement are determined, for example, by calculating an average of physiologic parameter measurements that are generated as described above. As a result, a short term average measurement STA(i) is equal to the sum of the previously calculated short-term average measurement STA(i-1) and the current calculated physiologic parameter (i), divided by the predetermined number of measurements associated with the measurement counter, Step 806.

For example, in an embodiment in which the physiologic parameter is generated from pressure measurements obtained by the implantable medical device, a short term average measurement STA(i) is equal to the sum of the previously calculated short-term average measurement STA(i-1) and the current calculated pressure parameter(i), divided by the predetermined number of measurements associated with the measurement counter. Similarly, in an embodiment in which the physiologic parameter is generated from heart rate activity measurements obtained by the implantable medical device, a short term average measurement STA(i) is equal to the sum of the previously calculated short-term average measurement STA(i-1) and the current calculated HRV parameter (i), divided by the predetermined number of measurements associated with the measurement counter. In the same way, in an embodiment in which the physiologic parameter is generated from activity level measurements obtained by the implantable medical device, a short term average measurement STA(i) is equal to the sum of the previously calculated short-term average measurement STA(i-1) and the current calculated activity parameter (i), divided by the predetermined number of measurements associated with the measurement counter.

Once the short term average measurement STA(i) is determined, the baseline measurement BL(i) is updated by being set equal to the short term average measurement STA(i), Step 808, and the physiologic parameter measurement counter is decremented, Step 810. Once a next valid physiologic parameter measurement is received, Step 811, a determination is made as to whether all physiologic parameter measurements have been made by determining whether the measurement counter is greater than zero, Step 812.

If all physiologic parameter measurements have not been made and therefore the measurement counter is determined to be greater than zero, YES in Step 812, the averaging process is repeated, Steps 820-812. It is understood that the present invention is not intended to be limited to the averaging scheme illustrated in Steps 802-812, and therefore the present invention is not intended to be limit to determining an average of the physiologic parameter using the averaging scheme illustrated in FIG. 9. Rather the average of the physiologic parameters may be calculated using any other known averaging scheme or schemes.

Once all physiologic parameter measurements have been made and therefore the initial values of the baseline BL measurement and the short term average STA measurement are determined, NO in Step 812, the short term average STA measurement and the baseline BL measurement are updated, Steps 814 and 816.

Figure 10:
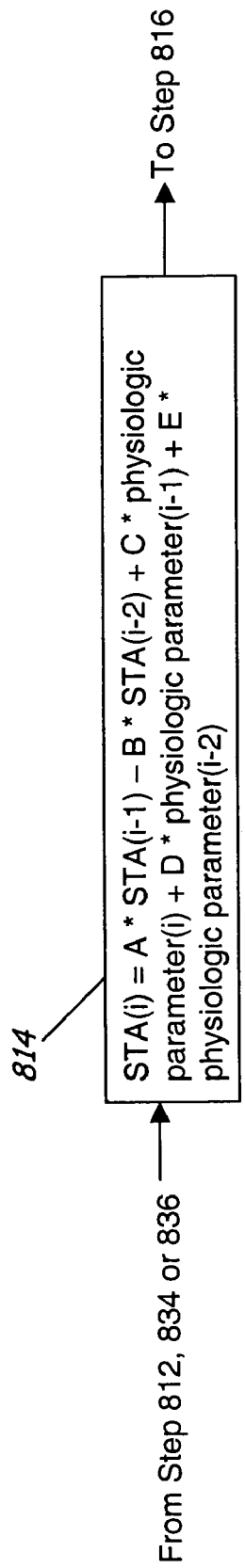
FIG. 10 is an exemplary schematic diagram illustrating updating of short term average measurement values, according to an embodiment of the present invention.

FIG. 10 is an exemplary schematic diagram illustrating updating of short term average measurement values, according to an embodiment of the present invention. As illustrated in FIG. 10, according to an embodiment of the present invention, the short term average measurement STA(i) is updated according to a second order low pass filter. In particular, the short term average STA(i) measurement is updated by taking a weighted sum of the short term average for the two previous days, A*STA(i-1) and B*STA(i-2), respectively, and the physiologic parameter measurement calculated for the current day, C*physiologic parameter (i), and the two previous days, D*physiologic parameter (i-1) and E*physiologic parameter (i-2), respectively.

By way of example, according to an embodiment of the present invention in which the physiologic parameter is generated from pressure measurements obtained by the implantable medical device, weighted variable A is equal to 1.1095, weighted variable B is equal to 0.4130, weighted variable C is equal to 0.1389, weighted variable D is equal to 0.0256 and weighted variable E is equal to 0.1389. According to an embodiment of the present invention in which the physiologic parameter is generated from heart rate variability measurements obtained by the implantable medical device, weighted variable A is equal to 1.1095, weighted variable B is equal to 0.4130, weighted variable C is equal to 0.1389, weighted variable D is equal to 0.0256 and weighted variable E is equal to 0.1389. According to an embodiment of the present invention in which the physiologic parameter is generated from activity measurements obtained by the implantable medical device, weighted variable A is equal to 0.3008, weighted variable B is equal to 0.1953, weighted variable C is equal to 0.2344, weighted variable D is equal to 0.4258 and weighted variable E is equal to 0.2344.

However, it is understood that according to the present invention, weighted variables A-E are not intended to be limited to these values, and the low pass filter is not intended to be limited to a second order low pass filter.

Figure 11:
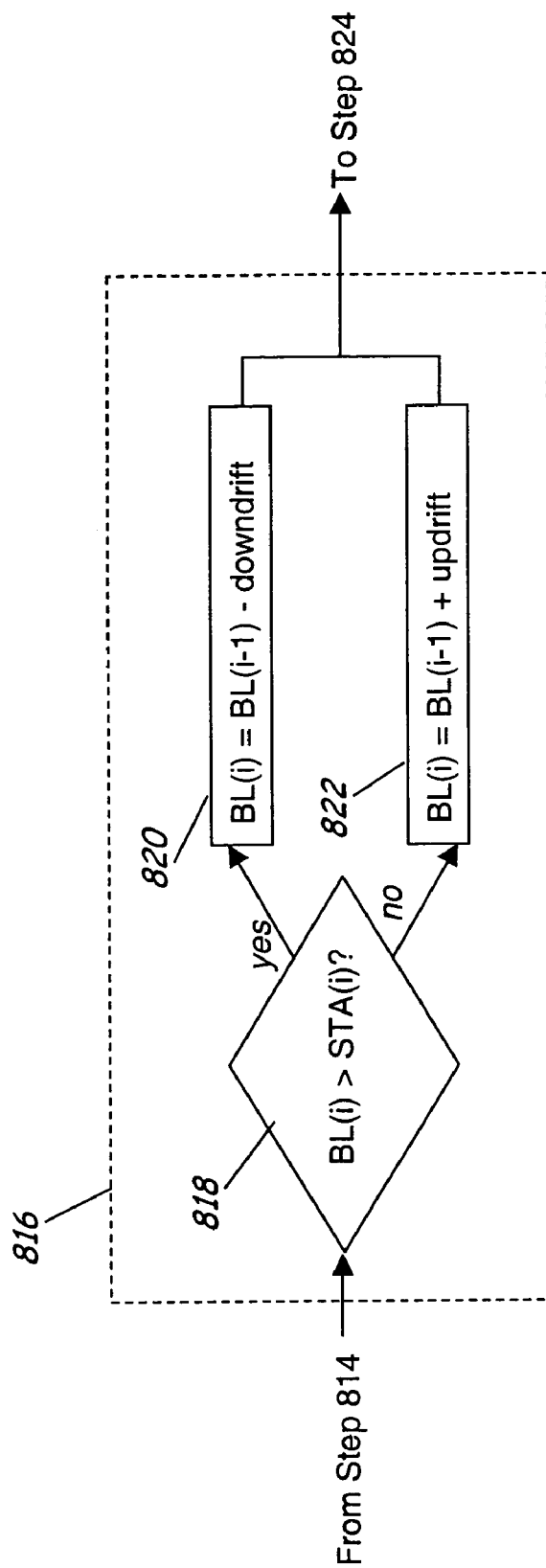
FIG. 11 is an exemplary schematic diagram illustrating updating of baseline measurement values, according to an embodiment of the present invention.

According to the present invention, the baseline measurement is updated at a much slower rate than the short term average measurement. FIG. 11 is an exemplary schematic diagram illustrating updating of baseline measurement values, according to an embodiment of the present invention. As illustrated in FIGS. 8 and 11, according to an embodiment of the present invention, during the updating of the baseline BL measurement in Step 816, once the short term average measurement is updated in Step 814, microprocessor 224 determines the location of the short term average measurement STA(i) relative to the current baseline measurement BL(i) by determining whether the baseline measurement BL(i) is greater than the short term average measurement STA(i), Step 818. If the current baseline measurement BL(i) is greater than the short term average measurement STA(i), YES in Step 818, the current baseline measurement BL(i) is updated by being set equal to the previous baseline measurement BL(i-1) reduced by a predetermined downdrift, Step 820. On the other hand, if the current baseline measurement BL(i) is not greater than the short term average measurement STA(i), NO in Step 818, the current baseline measurement BL(i) is updated by being set equal to the previous baseline measurement BL(i-1) increased by a predetermined updrift, Step 822.

According to the present invention, in order to make the implantable medical device more sensitive to decreases in measurements, the downdrift in Step 820 is set so as to be less than the updrift in Step 822. For example, although any desired updrift and downdrift values may be utilized, according to an embodiment of the present invention in which the physiologic parameter is generated from pressure measurements obtained by the implantable medical device, the downdrift is set to be approximately equal to 73/256 mmHG and the updrift is set to be approximately equal to 10/256 mmHG. According to an embodiment in which the physiologic parameter is generated from heart rate variability measurements obtained by the implantable medical device, the downdrift is set to be approximately equal to 26/256 ms and the updrift is set to be approximately equal to 53/256 ms. According to an embodiment in which the physiologic parameter is generated from activity measurements obtained by the implantable medical device, the downdrift is set to be approximately equal to 1/256 hours/day and the updrift is set to be approximately equal to 4/256 hours/day. The method of updating the value of the baseline BL measurement could also be based upon lowpass filters with either the current measurement or the short term average STA measurement as the input. The inventors have determined that a faster rate of growth than decline of BL is advantageous for predicting hospitalizations for heart failure decompensation while avoiding false alarms for those variables where decline in the physiologic parameter is associated with decompensation, such as heart rate variability and activity. On the other hand, for physiologic parameters such as ePAD, where an increase in the parameter is associated with decompensation, a faster rate of decline than growth of the baseline measurement is advantageous.

Returning to FIG. 8, once the short term average measurement and baseline measurement have been updated, microprocessor 224 determines whether the relative position of the short term average measurement and the baseline measurement has changed, such as would occur if either the short term average measurement was less than the baseline measurement but is now greater than or equal to baseline measurement, or the short term average measurement was greater than the baseline measurement but is now less than or equal to baseline measurement, Step 824. In particular, as illustrated in FIG. 7A for example, since a calculated short term average measurement 403 corresponding to the previous day is less than the baseline measurement 402, and a calculated short term measurement 405 corresponding to the current day is greater than the baseline measurement 402, the short term average measurement 404 crosses the baseline measurement 402, YES in Step 824. On the other hand, since a calculated short term average measurement 407 corresponding to the previous day is greater than the baseline measurement 402, and a calculated short term measurement 409 corresponding to the current day is less than the baseline measurement 402, the short term average measurement 404 crosses the baseline measurement 402, YES in Step 824. Such crossing of the baseline measurement 402 by the short term average measurement 404 is an indication that there is no longer any evidence to suspect the existence of an abnormal pressure parameter, indicative of heart failure decompensation.

As illustrated in FIG. 8, if it is determined that short term average measurement crosses baseline measurement, YES in Step 824, microprocessor 224 sets the integral of the difference between the physiologic parameter and the baseline measurement (IntDiff) equal to zero, Step 826. On the other hand, if it is determined that short term average measurement does not cross baseline measurement, NO in Step 824, microprocessor 224 updates the integral of the difference between the physiologic parameter and the baseline measurement (IntDiff) by adding the current difference between the current calculated physiologic parameter and the baseline parameter, Step 828. A determination is then made as to whether significant changes in the physiologic parameter have occurred, Step 830.

According to an embodiment of the present invention, the determination in Step 830 as to whether a significant change in the physiologic parameter has occurred is made, for example, by determining whether the updated integral of the difference between the physiologic parameter and the baseline measurement (IntDiff) is less than a predetermined IntDiff threshold 416, 516, 616. According to another embodiment of the present invention, the determination in Step 530 as to whether a significant change in the physiologic parameter has occurred can be made by determining whether the difference between the short term average measurement and the baseline measurement STA-BL is less than a predetermined threshold 418, 518, 618, by determining whether the baseline measurement is less than a predetermined baseline measurement threshold 420, 520, 620, or by determining whether any combination of IntDiff, STA-BL and the baseline measurement is less than the respective thresholds.

The parameter corresponding to the difference between the short term average measurement and the baseline measurement STA-BL is similar to that described in U.S. Patent No. 5,957,861 to Combs et al., incorporated herein by reference in its entirety, and is a less useful indicator of the presence of significant change in the physiologic parameter, when the measured physiologic parameter declines slowly for weeks before hospital admission. However, the STA-BL parameter may be useful in those patients with very rapid decompensation of heart failure. Finally, the direct thresholding of the BL parameter is the simplest programmed threshold and may have value for detecting extremely slow disease processes.

If it is determined that a significant change in the physiologic parameter has occurred, YES in Step 830, an alarm or patient indicator is activated, via patient notification circuit 331, to inform the patient of the condition, Step 832. For example, an alarm is activated when the difference between the calculated short term average measurement and the calculated baseline measurement as a percentage of the baseline measurement generated in one of plot 410, 510, 610 (FIGS. 7A-7C) is less than threshold 418, 518, 618 or when IntDiff generated in one of plot 414, 514, 614 is less than threshold 416, 516, 616, or when the baseline BL measurement is less than a predetermined baseline measurement threshold. It is understood that the values of thresholds 416, 516, 616 and 418, 518, 618 are programmable, are therefore are not intended to be limited to the values illustrated in FIGS. 7A-7C. In the same way, baseline measurement threshold 420, 520, 620 is patient specific and therefore may be preprogrammed by the clinician to any value deemed appropriate for a specific patient.

According to the present invention, the alarm of Step 832 could include an audible alarm, vibration, stimulation, communication to an external device via telemetry circuitry 330 for transmission to an external database or communication network, for example. According to an embodiment of the present invention, in addition to merely alerting the patient and/or an outside entity of the detection of heart failure decompensation based on changes in the physiologic parameter, a therapy may also be initiated or modified, Step 833, in response to the detection of decompensation based on changes in the physiologic parameter. Such therapies could include, for example, a drug pump, a pacing mode, a pacing rate, cardiac resynchronization therapy (CRT), cardiac potentiation therapy (CPT), etc. In addition, according to an embodiment of the present invention, the algorithm for detecting changes in a physiologic parameter could also be modified, Step 833, in response to the detection of decompensation based on changes in the physiologic parameter. For example, the number of times that the physiologic parameter is generated could be increased to a faster rate from the initial rate, i.e., from once per day to once an hour.

Whether or not therapy is initiated or modified or the algorithm for detecting changes in the physiologic parameter is modified in response to determining changes in the physiologic parameter is programmable and therefore optional. As a result, once the alarm has been activated, Step 832, a determination is made as to whether a therapy or the algorithm for detecting changes in the physiologic parameter should be modified or initiated, Step 833. If so, the therapy and/or the algorithm for detecting changes in the physiologic parameter is initiated or modified, Step 835. Once either the alarm has been activated in Step 832 and no therapy/algorithm modification/initiation is set, NO in Step 833, or the alarm has been activated and a therapy/algorithm has been modified or initiated, YES in Step 833 and Step 835, or once it is determined that a significant change in the physiologic parameter has not occurred, NO in Step 830, the process waits for the next valid physiologic parameter to be generated, Step 834, and the process of Steps 814-832 is repeated.

Once the IntDiff parameter 412, 512, 612 has exceeded the predetermined threshold and an alert has been issued, the alert will continue to activate each day until IntDiff parameter is cleared, Step 826. Clearing of IntDiff parameter occurs when the short term average STA crosses over the baseline BL measurement, indicating that there is no longer evidence of an abnormal physiologic parameter. Cessation of the alarm condition as stated above is advantageous to the clinician and patient, because it can be used to indicate that the corrective action that was taken upon initiation of the alert condition (e.g., increased dose of a diuretic) was successful in correcting the condition.

According to an embodiment of the present invention, once the next valid physiologic parameter is generated, Step 834, a determination is made as to whether a command has been received via telemetry circuit 330 to reset the algorithm, Step 836. This feature is optional and is convenient for establishing new initial values of BL and STA after an intervention that rapidly changes the measured physiologic parameter (such as administration of intravenous diuretics). The user can command the algorithm to reset immediately, or to reset after a programmable delay (e.g., 1 week). The delay is useful to force a reset only after the patient's status is predicted to stabilize, such as after ingestion of medication by the patient, for example. The command to reset the algorithm can be received using the activation describe, for example, in commonly assigned U.S. Pat. No. 5,836,975 to DeGroot et al., incorporated herein by reference in its entirety.

Figure 12:
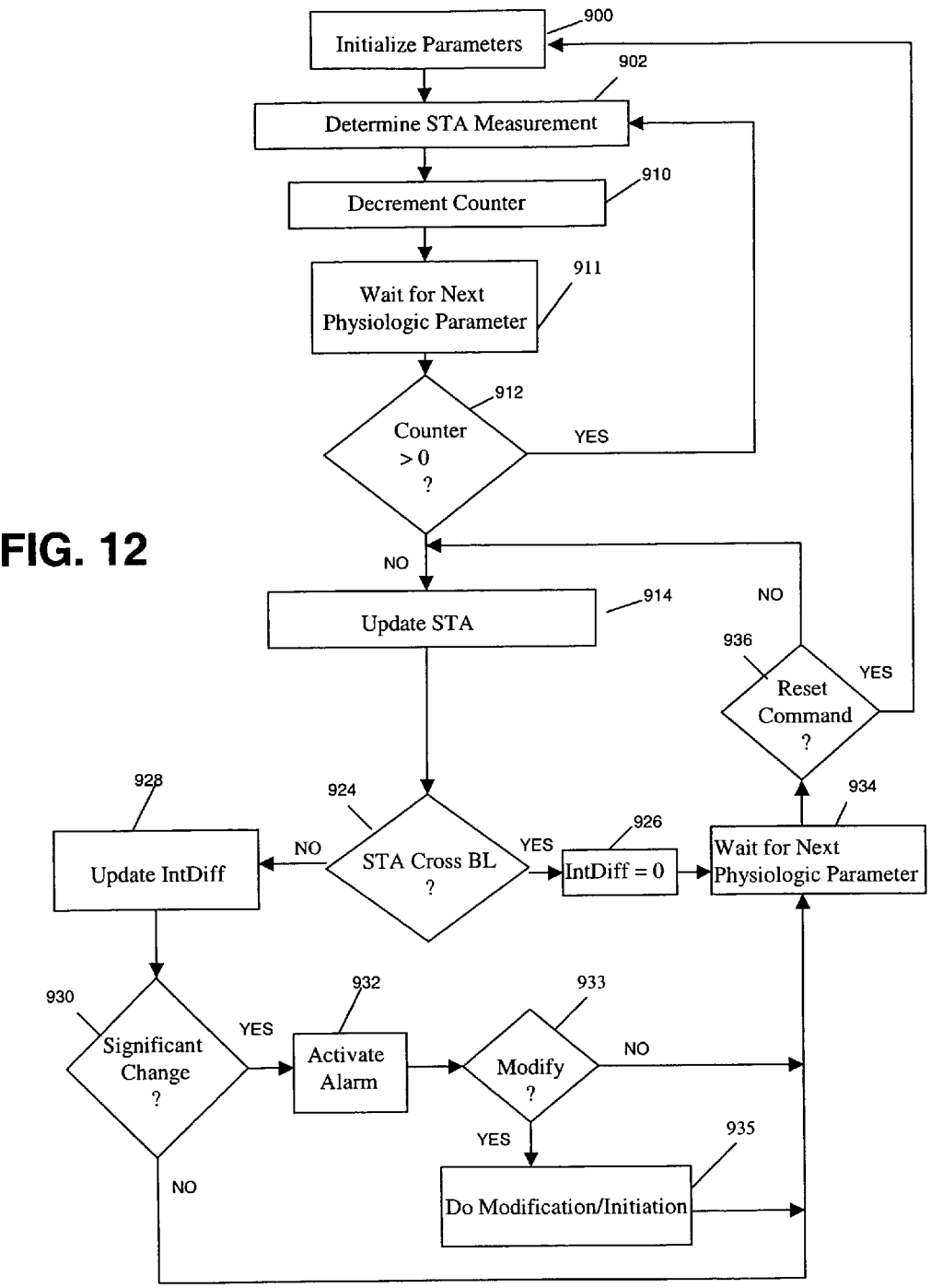
FIG. 12 is a flowchart of a method illustrating a method for determining changes in a physiologic parameter according to an embodiment of the present invention.

FIG. 12 is a flowchart of a method illustrating a method for determining changes in a physiologic parameter according to an embodiment of the present invention. The method for determining changes in a physiologic parameter illustrated in FIG. 12 is similar to the method described above in reference to FIG. 8, however, during initialization of Step 900 in the embodiment of FIG. 12, the baseline measurement is set equal to a predetermined value, Step 908, input by the physician during implant of the device. The baseline measurement then maintains this predetermined value throughout the process of determining changes in the physiologic parameter, rather than being updated automatically in response to the calculated physiologic parameter. As a result, the step of updating the baseline measurement, Step 816, in the embodiment of FIG. 8 is not included in the embodiment of FIG. 12.

FIG. 13 is an exemplary schematic diagram illustrating obtaining initial short term average measurement values, according to an embodiment of the present invention. As illustrated in FIG. 13, since the baseline measurement maintains the predetermined value obtained during initializtion, Step 900, the embodiment of FIG. 12 differs from the embodiment of FIG. 8 in that once the parameters are initialized, Step 900, an initial value is determined only for the short term average measurement, Step 906, and not for the baseline measurement.

In addition, in the embodiment of FIG. 12, the determination of whether a significant change has occurred is made in Step 930 by determining whether the updated integral of the difference between the physiologic parameter and the baseline measurement (IntDiff) is less than predetermined IntDiff threshold 416, 516, 616. According to another embodiment of the present invention, the determination in Step 930 as to whether a significant change in the physiologic parameter has occurred can be made by determining whether the difference between the short term average measurement and the baseline measurement STA-BL is less than a predetermined threshold 418, 518, 618 and in yet another embodiment by determining whether any combination of IntDiff and STA-BL is less than the respective thresholds 416, 516, 616 and 418, 518 618. The remainder of the steps involved in the embodiment of FIG. 12 are similar to the corresponding steps described above in reference to the embodiment of FIG. 8, and therefore are not repeated merely for the sake of brevity.

By maintaining the selected predetermined value for the baseline measurement through the process, the embodiment of FIG. 12 enables a clinician who is familiar with the specific physiologic tendencies of a patient and who desires to have the ability to set the baseline measurement for that patient at a specific predetermined value so that the baseline measurement maintains that predetermined value throughout the process of determining change in the physiologic parameter according to the present invention.

Some of the techniques described above may be embodied as a computer-readable medium comprising instructions for a programmable processor such as microprocessor 224 or pacer timing/control circuitry 212 shown in FIG. 4. The programmable processor may include one or more individual processors, which may act independently or in concert. A "computer-readable medium" includes but is not limited to any type of computer memory such as floppy disks, conventional hard disks, CR-ROMS, Flash ROMS, nonvolatile ROMS, RAM and a magnetic or optical storage medium. The medium may include instructions for causing a processor to perform any of the features described above for initiating a session of determining the change in the physiologic parameter according to the present invention.

While a particular embodiment of the present invention has been shown and described, modifications may be made. It is therefore intended in the appended claims to cover all such changes and modifications, which fall within the true spirit and scope of the invention.

What is claimed is:

1. An implantable medical device for detection of changes in physiologic parameters, comprising:
   means for generating measured physiologic parameters;
   means for generating an adaptive baseline trend of the measured physiologic parameters corresponding to a first time period;
   means for generating a short term trend of the measured physiologic parameters corresponding to a second time period less than the first time period;
   means for generating a metric of physiologic parameter change between the adaptive baseline trend and one of a most recent measured physiologic parameter and the short term trend of the measured physiologic parameters; and
   means for updating the adaptive baseline trend by setting the adaptive baseline trend equal to a previous adaptive baseline trend reduced by a predetermined downdrift in response to the current adaptive baseline trend being greater than the current short term trend, and by setting the adaptive baseline trend equal to the previous adaptive baseline trend increased by a predetermined updrift in response to the current adaptive baseline trend being less than the current short term trend, the downdrift and the updrift having respective first values in response to a decline in the measured physiologic parameters being associated with decomposition, and respective second values different from the first values in response to an increase in the measured physiologic parameters being associated with decomposition.

2. The implantable medical device of claim 1, wherein the updrift is greater than the downdrift.

3. The implantable medical device of claim 1, wherein the downdrift is greater than the updrift.

4. A method for detection of changes in physiologic parameters a patient, comprising:
   generating measured physiologic parameters;
   generating an adaptive baseline trend of the measured physiologic parameters corresponding to a first time period;
   generating a short term trend of the measured physiologic parameters corresponding to a second time period less than the first time period;
   generating a metric of physiologic parameter change between the adaptive baseline trend and one of a most recent measured physiologic parameter and the short term trend of the measured physiologic parameters; and
   updating the adaptive baseline trend by setting the adaptive baseline trend equal to a previous adaptive baseline trend reduced by a predetermined downdrift in response to the current adaptive baseline trend being greater than the current short term trend, and by setting the adaptive baseline trend equal to the previous adaptive baseline trend increased by a predetermined updrift in response to the current adaptive baseline trend being less than the current short term trend, the downdrift and the updrift having respective first values in response to a decline in the measured physiologic parameters being associated with decomposition, and respective second values different from the first values in response to an increase in the measured physiologic parameters being associated with decomposition.

5. The method of claim 4, wherein the updrift is greater than the downdrift.

6. The method of claim 4, wherein the downdrift is greater than the updrift.

* * * * *